: US 9,842,414 B2
(45) Date of Patent: Dec. 12, 2017

(12) United States Patent
Koehler et al.

(54) MONOCHROMATIC ATTENUATION CONTRAST IMAGE GENERATION BY USING PHASE CONTRAST CT

(71) Applicant: KONINKLIJKE PHILIPS N.V., Eindhoven (NL)

(72) Inventors: Thomas Koehler, Norderstedt (DE); Ewald Roessl, Henstedt-Ulzburg (DE); Dirk Schafer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 118 days.

(21) Appl. No.: 14/907,084

(22) PCT Filed: Jul. 23, 2014

(86) PCT No.: PCT/EP2014/065767
§ 371 (c)(1),
(2) Date: Jan. 22, 2016

(87) PCT Pub. No.: WO2015/014677
PCT Pub. Date: Feb. 5, 2015

(65) Prior Publication Data
US 2016/0163072 A1 Jun. 9, 2016

(30) Foreign Application Priority Data

Jul. 30, 2013 (EP) .................................. 13178573

(51) Int. Cl.
*G06K 9/00* (2006.01)
*G06T 11/00* (2006.01)
(Continued)

(52) U.S. Cl.
CPC ............ *G06T 11/005* (2013.01); *A61B 6/032* (2013.01); *A61B 6/461* (2013.01); *A61B 6/467* (2013.01);
(Continued)

(58) Field of Classification Search
CPC ....... G01N 2223/045; G01N 2223/423; G01N 23/046; G01N 23/20075; G06T 11/005;
(Continued)

(56) References Cited

U.S. PATENT DOCUMENTS 4,029,963 A    6/1977   Alvarez
9,613,441 B2 * 4/2017   Koehler ............... G06T 11/006
(Continued)

FOREIGN PATENT DOCUMENTS

EP          2437051       4/2012
WO       2009/113713       9/2009
(Continued)

OTHER PUBLICATIONS

McDonald, "Advanced phase-contrast imaging using a grating interferometer", J. Synchrotron Rad. (2009) 16, 562-571.
(Continued)

*Primary Examiner* — Tom Y Lu

(57) ABSTRACT

The present invention relates to a method and apparatus for X-ray phase contrast imaging. The method comprises the following steps: from the measured phase gradient and overall attenuation information, an electron density is computed; the contribution $p_c$ of the Compton scattering to the overall attenuation is estimated from the electron density; the contribution pp of the photo-electric absorption to the overall attenuation is estimated from the overall attenuation and the contribution $p_c$; the values $p_c$ and $p_p$ are used to reconstruct a Compton image and a photo-electric image; by linear combination of these two images, a monochromatic image at a desired energy is obtained.

14 Claims, 3 Drawing Sheets

(51) Int. Cl.
    *A61B 6/00*    (2006.01)
    *G01N 23/20*   (2006.01)
    *G01N 23/04*   (2006.01)
    *A61B 6/03*    (2006.01)
(52) U.S. Cl.
    CPC ............ *A61B 6/484* (2013.01); *A61B 6/5205* (2013.01); *A61B 6/5235* (2013.01); *G01N 23/046* (2013.01); *G01N 23/20075* (2013.01); *A61B 6/4035* (2013.01); *A61B 6/4241* (2013.01); *A61B 6/4291* (2013.01); *G01N 2223/045* (2013.01); *G01N 2223/423* (2013.01); *G06T 2207/10081* (2013.01); *G06T 2207/10124* (2013.01); *G06T 2207/30008* (2013.01); *G21K 2207/005* (2013.01)
(58) Field of Classification Search
    CPC . G06T 2207/10081; G06T 2207/10124; G06T 2207/30008; A61B 6/032; A61B 6/4035; A61B 6/4241; A61B 6/4291; A61B 6/461; A61B 6/467; A61B 6/484; A61B 6/5205; A61B 6/5235
    See application file for complete search history.

(56) References Cited

U.S. PATENT DOCUMENTS

| | | |
|---|---|---|
| 2008/0095302 A1 | 4/2008 | Ruhrnschopf |
| 2008/0317320 A1 | 12/2008 | Van Stevendaal |
| 2009/0161939 A1 | 6/2009 | Wu et al. |
| 2013/0032715 A1* | 2/2013 | Zhu .......... G21K 1/02 250/309 |
| 2015/0117595 A1* | 4/2015 | Flohr .......... A61B 6/482 378/5 |
| 2015/0243397 A1* | 8/2015 | Yun .......... G01N 23/20075 378/36 |

FOREIGN PATENT DOCUMENTS

| | | |
|---|---|---|
| WO | 2011/145040 | 11/2011 |
| WO | 2012/029039 | 3/2012 |
| WO | 2013/011418 | 1/2013 |

OTHER PUBLICATIONS

Alvarez, et al., "Energy-selective reconstructions in the X-ray computerized tomography", Phys. Med. Biol., vol. 21, No. 5, 733-744; Jan. 1, 1976.

Donath, et al., "Towards Clinical X-Ray Phase-Contrast CT:Demonstration of Enhanced Soft-Tissue Contrast in Human Specimen", Invest Radiol, 2010.

Casteele, et al., "A bimodal energy model for correcting beam hardening artefacts in X-ray tomography", 2003 IEEE.

* cited by examiner

MONOCHROMATIC ATTENUATION CONTRAST IMAGE GENERATION BY USING PHASE CONTRAST CT

CROSS REFERENCE TO RELATED APPLICATIONS

This application is the U.S. National Phase application under 35 U.S.C. §371 of International Application No. PCT/EP2014/065767, filed Jul. 23, 2014, published as WO 2015/014677 on Feb. 5, 2015, which claims the benefit of European Patent Application Number 13178573.5 filed Jul. 30, 2013. These applications are hereby incorporated by reference herein.

FIELD OF THE INVENTION

The invention relates to a method for generating an image, to an image processing system, to a computer program element, and to a computer readable medium.

BACKGROUND OF THE INVENTION

There is an increasing interest in 3D X-ray imaging to move towards quantitative imaging. One route that is pursued is the use of dual energy (or even energy resolving) acquisition schemes in order to provide quantitative, mono-chromatic images.

U.S. Pat. No. 4,029,963 A discloses projection measurements made of the transmitted x-ray beam in low and high energy regions. Such projection measurements are combined in a non-linear processor to produce atomic-number-dependent and density-dependent projection information. This information is used to provide cross-sectional images which are free of spectral-shift artifacts and completely define the specific material properties. WO 2009/113713 A1 discloses a computing unit that computationally determines a quantity of an X-ray phase attributable to the object of examination and an X-ray transmittance of the object of examination from data detected by the detector. WO 2011/145040 A1 relates to an image processing apparatus for filtering an image. Said apparatus comprises an image input for obtaining a first and a second image of the same object, the first and second images comprising a plurality of voxels and being interrelated by a noise covariance, each voxel having a voxel value including a signal value and a noise value. EP 2 437 051 A1 discloses pseudo dual-energy material identification systems and methods with under-sampling.

SUMMARY OF THE INVENTION

There may therefore be a need for a method and related apparatus or system for image generation.

The object of the present invention is solved by the subject matter of the independent claims where further embodiments are incorporated in the dependent claims. It should be noted that the following described aspect of the invention equally apply to the image processing system, to the computer program element and to the computer readable medium.

According to a first aspect of the invention there is provided a method for generating an image, comprising the following steps of:

receiving a phase-contrast image recording phase gradient and overall attenuation information (that is, the attenuation as actually measured at a detector);

computing an electron density image based on the phase gradient information as recorded in the phase-contrast image;

estimating, from the estimated electron-density, a contribution, $p_C$, of the Compton scattering to the recorded overall attenuation;

estimating the contribution, $p_p$, of the photo-electric scattering to the attenuation;

for a specified energy, combining the $p_C$ and $p_p$ into an essentially mono-chromatic image for the specified energy.

According to one embodiment, the method further comprises displaying the mono-chromatic image on a display device.

According to one embodiment, the method further comprises: responsive to a request including a new desired energy specification, repeating the previous steps for the new energy, and displaying a new mono-chromatic image on the display device for the new energy.

Resolving the received phase contrast imagery for $p_p$ and $p_C$ as proposed herein amounts in essence to eliminating beam hardening effects on both imaging "channels", namely in the phase contrast image and in the attenuation contrast image. This affords quantitative imaging on both channels even with an energy integrating detector. A photon counting detector capable of energy discrimination as used in spectral imaging is not required. The proposed methods may therefore be considered a beam hardening elimination where images generated during the processing are used to generate monochromatic attenuation contrast images.

According to one embodiment, the method further comprises: responsive to request for a visualization mode, rendering the monochromatic image or the new mono-chromatic image accordingly and effectuating display of same on the display unit. This allows adding a back-end functionality to scanners with energy integrating detectors that were previously available only in dual energy/spectral CT. The method provides means to display "monochromatic images" at almost arbitrary, used selected energies.

According to one embodiment, the visualization mode includes water-bone image rendering or water-iodine rendering.

According to one embodiment, the phase-contrast image is registered at an energy integrating detector.

According to one embodiment, the phase-contrast image is recorded with a radiography imaging apparatus.

According to one embodiment, the phase-contrast image is recorded with a computed tomography, CT, imaging apparatus.

According to one embodiment, the method is executed within a framework of a beam-hardening correction algorithm. This allows saving CPU time and/or memory resources.

The proposed method allows using phase contrast as an additional contrast mechanism, with the potential benefit to increase the sensitivity of an energy integrating X-ray system, CT or 2D radiography.

According to a second aspect of the invention there is provided an image processing system method for generating an image, such image processing system comprising an imaging apparatus configured to supply the phase-contrast image; a user input device for receiving the desired energy specification; a processing unit configured to process the phase-contrast image according to any embodiment of the method according to the invention; and a display unit for displaying the monochromatic image computed by the processing unit.

According to one embodiment, the image processing system is arranged for displaying the mono-chromatic image on the display device.

According to one embodiment, the image processing system is arranged for enabling a user to enter a request including an updated energy specification; repeating the step of combining $p_C$ and $p_p$ into a mono-chromatic image responsive to said request for the updated energy specification; and displaying an updated mono-chromatic image on the display device for the updated energy specification.

According to one embodiment, the image processing system is arranged for enabling a user to enter a request for a visualization mode; and rendering responsive to said request the monochromatic image or the updated monochromatic image accordingly and effectuating display of same on the display device.

According to one embodiment, the image processing system is arranged for enabling a user to enter a request for a visualization mode including water-bone image rendering and water-iodine rendering; and rendering responsive to said request the monochromatic image or the updated mono-chromatic image accordingly and effectuating display of same on the display device.

According to one embodiment, the image processing system is arranged for recording the phase-contrast image using an energy integrating detector.

According to one embodiment, the imaging apparatus is a computed tomography imaging apparatus.

According to one embodiment, the image processing system is arranged for executing any embodiment of the method within a framework of a beam-hardening correction algorithm.

According to a third aspect of the invention there is provided a computer program for controlling any embodiment of the image processing system according to any—, which, when being executed by a processing unit, is arranged for performing any embodiment of the method.

According to a fourth aspect of the invention there is provided a computer readable medium having stored thereon the computer program.

Definitions

Image data is referred to herein as "quantitative", if the respective image values carried by the individual image elements (voxel or pixels) making up the image, vary directly, at true inter-pixel/voxel scaling, with the attenuation experienced by X-ray radiation at a specified energy when passing through portions of the imaged object that correspond to the respective image elements. In other words, the recorded image values scale across the whole image only in respect of the attenuation experienced by radiation having the specific energy at the exclusion of distortive effects, such as, in particular, beam hardening effects. In yet other words, the image values across the whole image are comparable with each other in respect of attenuation at the specific energy.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
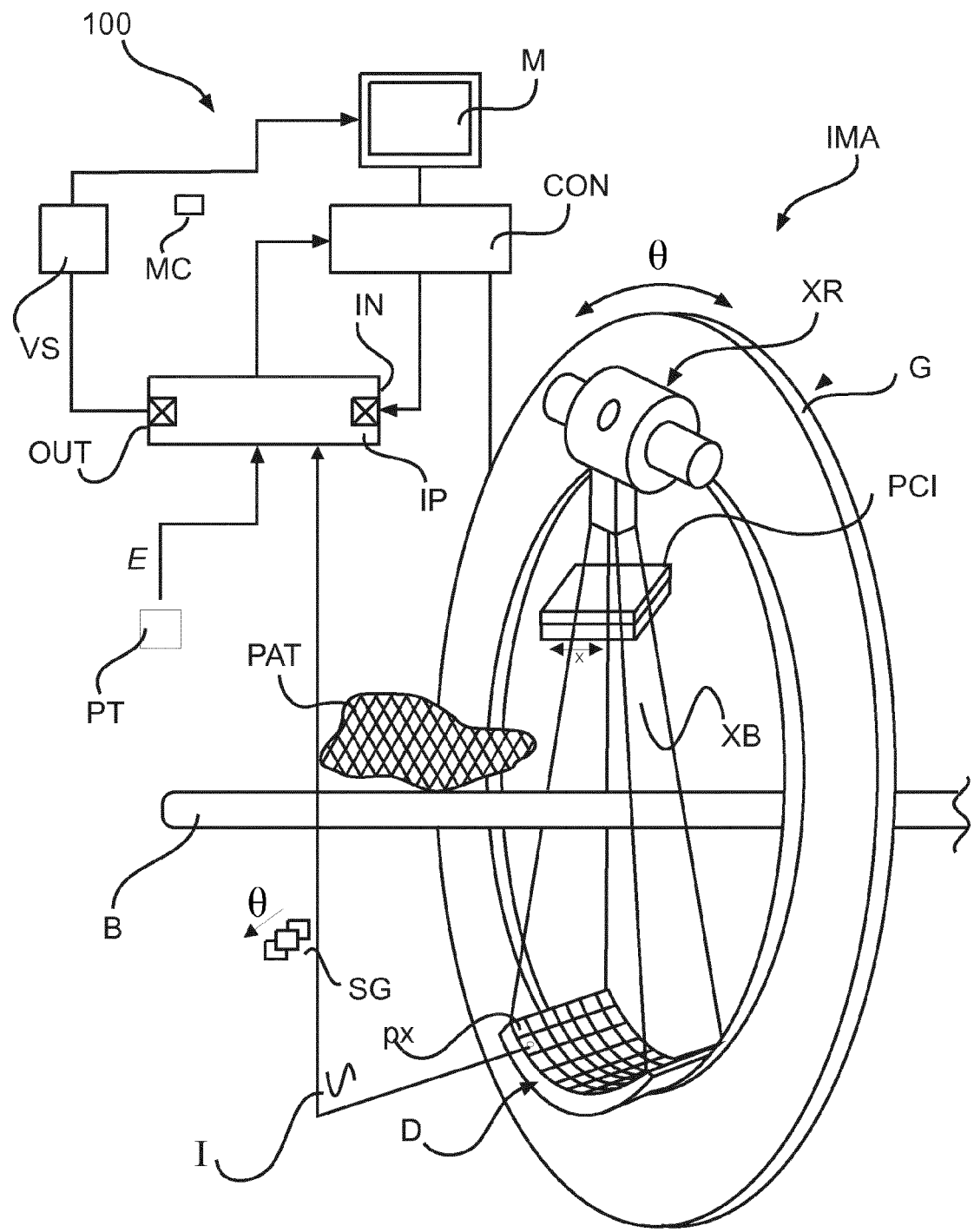
FIG. 1 shows an imaging arrangement.

With reference to FIG. 1, there is shown an imaging apparatus employed in one embodiment of the image processing system according to the invention. Broadly said imaging apparatus includes an X-ray based CT scanner IMA and a workstation or operating console CON for controlling operation of said scanner IMA.

A general purpose computing system may serve as the operator console CON, and includes an output device such as a display M and an input device such as a keyboard, mouse, and/or the like. Software resident on the console CON allows the operator to control the operation of the X-ray based CT scanner IMA, for example, allowing the operator to select imaging parameter directly or indirectly through selecting a pre-generated imaging protocol. Display unit (such as a monitor/screen) M is communicatively coupled to console CON to aid inputting control information or to view operational sates of the scanner or to view images supplied by the scanner or of images obtained by image processing the so supplied images. There is also an image processing unit IP that is in one embodiment communicatively coupled to console CON to effect said image processing. Broadly, processing unit IP includes input IN, EG and output OUT interfaces. Operation of image processing unit IP will be explained in more detail further below at FIG. 3.

Image rendering for images to be displayed on screen M is by a visualizer VS that is configured to receive image data and visualization information (as will be explained in more detail below at FIG. 3) to drive a video card of console CON to so effect display on screen M.

The scanner IMA includes a stationary gantry and a rotating gantry G, which is rotatably supported by the stationary gantry. The rotating gantry G rotates around an examination region, about a longitudinal or z-axis. The examination region is formed as an opening or bore in the rotating gantry G.

A subject support BD0, such as a couch, supports a subject PAT or object in the examination region and can be used to position the subject or object with respect to x, y, and/or z axes before, during and/or after scanning.

A radiation source XR, such as an X-ray tube ("tube"), is supported by the rotating gantry 104 and rotates with the rotating gantry G about the examination region, and emits radiation, via a focal spot, that traverses the examination region.

The radiation beam is centered about an iso-center of the bore and defines a generally circular shaped field of view FoV (of the scanner) to reconstruct for a transverse reconstruction plane, which is generally perpendicular to a center ray of the beam and which extends through the iso-center.

A radiation sensitive detector array D is located opposite the radiation source XR, across the examination region. The detector array D includes one or more rows of detector pixels or cells DCL that detect radiation traversing the examination region and generate an electrical current or voltage signal indicative of the detected radiation. The detector pixels are formed form integrating detectors according to one embodiment.

Rotation of rotatable gantry (and thus of at least the X-ray source's focal spot—in a fourth generation scanner it is only the tube that rotates in the gantry, with the detector array fixedly arranged to line all of the inside of the gantry to that at least a part of the detector can receive radiation for any rotation angle), is effected by one more controllers and/or one or more drive systems (e.g., a motor, a coupling, etc.).

During an imaging run when the scanner is in use, focal spot rotates over a predetermined angular range on a path (in general an arc or a full circular rotation) around bore B and hence subject or object PAT therein at a given angular frequency during a scan of the subject or object. For each rotation angle φ, the detector detects the radiation emitted by the focal spot after passage through the subject or object at said angle. The radiation experiences attenuation during passage through the subject or object with said attenuation proportional to the local densities of the subject or object. Each cell DCL (opposite focal spot) that is struck by an individual ray (of which said radiation beam is made up) responds by issuing a corresponding electric signals briefly mentioned above. The collection of said signals is then translated by a data acquisition system DAS (not shown) into a respective digital value representative of said attenuation. The collection of the so registered digital values for each (X-)ray are then consolidated into an array of digital values forming a 2D (two-dimensional) X-ray projection image for a given acquisition time and projection angle θ. The detector thereby records a collection of projection images, one or more for each rotation angle θ.

The workstation includes a reconstructor module to run a reconstruction algorithm (such as filtered back-projection FBP) that allows reconstructing the collection of projection images (sinogram) SG to generate cross sectional images ("slice (image)") for each axial position z. The collection of trans-axial slice images can then be combined by suitable renderer modules into volumetric image data indicative of the examination region and the portion of the subject or object therein.

As further shown in FIG. 1, the imaging scanner CT includes phase contrast imaging equipment PCI which allows extracting phase shift gradients from the recorded projection images. This is because, on top of the attenuation suffered by the X-ray in its passage through matter PAT, there is also phase shift φ caused by intervening matter PAT and the amount of which is described by the phase gradient.

Figure 2:
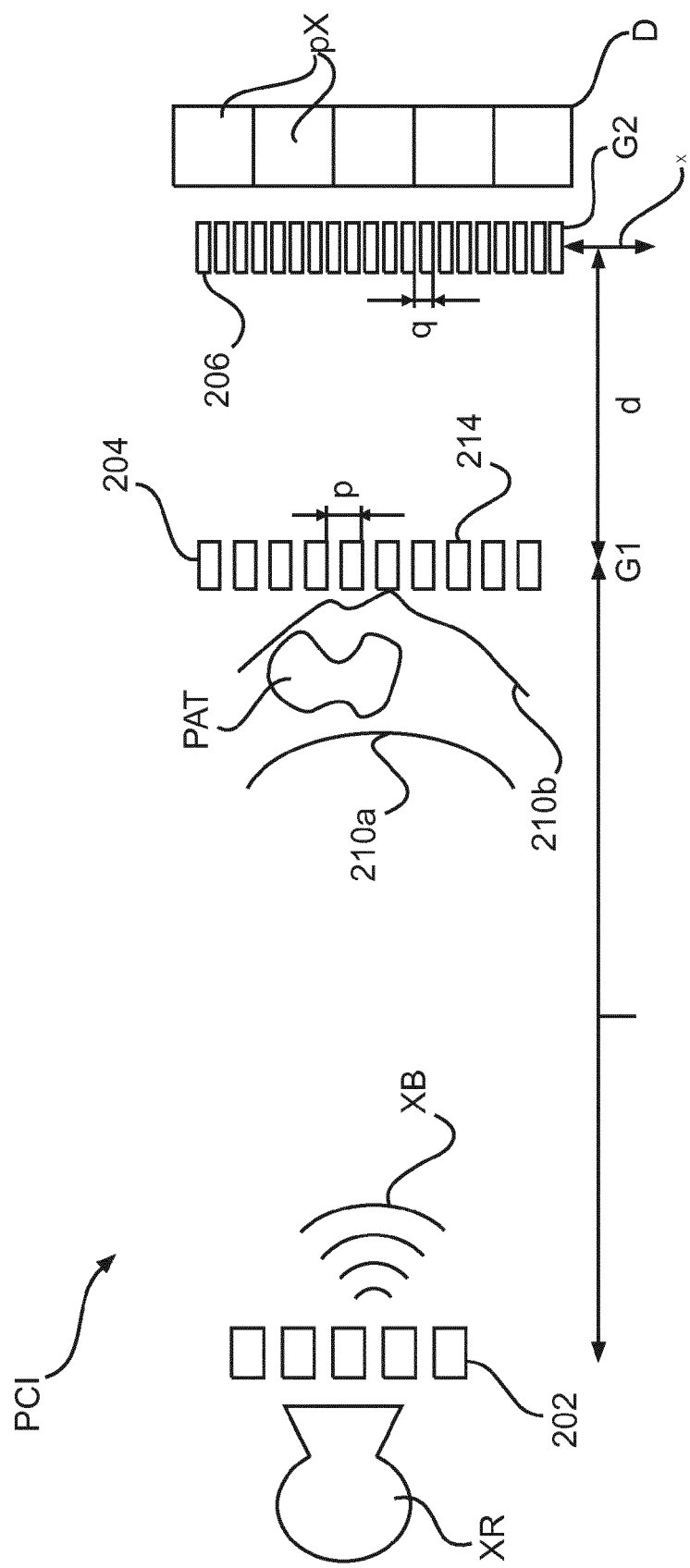
FIG. 2 shows phase contrast imaging equipment as used in the arrangement according to FIG. 1.

The basic components of the phase contrast imaging equipment PCI, essentially an interferometer, are described with reference to FIG. 2. In FIG. 2, X-ray source XR is depicted having a source grating element 202 arranged adjacently. X-ray radiation 114 penetrating source grating element 202 may be considered to be at least partially spatially coherent. X-ray radiation 114 comprises individual wave fronts of which wave front 210a is depicted as a wave front before penetration of object 108 while wave front 210b is depicted after penetration of object PAT, having an illustrated phase-shift.

Arranged after object PAT and spaced apart from both the detector element 104 and an analyzer grating $G_2$ 206 by distance d, is phase grating 204 having a pitch g. Detector D, with its individual detector pixel elements 116, subsequently detect an interference pattern of X-ray radiation XR, imposed by phase grating $G_1$ 204 and analyzer grating $G_2$ 206.

Actuator element 208 is schematically illustrated being adapted to laterally displace analyzer grating $G_2$ 206 relative to X-ray tube XR with source grating 202, phase grating $G_1$ 204 and X-ray detector 104. However, actuator element 208 may be arranged at any of the grating elements 202, 204, 206 for displacement x. Said actuator is used to effect what is known as "phase stepping". In phase stepping, one of the source grating, employed for generating the at least partly spatial coherent X-ray radiation, the phase grating, and the analyzer grating is displaced laterally with respect to the other gratings and the X-ray detector element by a fraction of its respective grating pitch, e.g., a fourth, sixth, or eighth of the grating pitch of the respective grating element constituting a phase stepping state. Image acquisition and lateral displacement is repeated, e.g., four, six, or eight times, for acquiring a plurality of phase contrast projections, constituting together a phase stepping series.

The phase-shift of the X-rays may be considered to be directly related to the integral of the electron density along the path of X-ray radiation. Grating-based differential phase-contrast imaging may allow employing a relatively broad-banded X-ray source, e.g., with ΔE/E~10%. In other words, polychromatic X-ray radiation rather than monochromatic X-ray radiation having substantially only a single wavelength may be employed for phase-contrast imaging.

The output of the phase contrast system imaging system IMA+PCI is comprised of three types of images: the attenuation contrast image, the phase contrast image, and the small angle scatter image (the small angle scattering is related to the loss of coherences of the X-ray beam. It is caused by object structures smaller than the detector pixel. However, the small angle scattering effect in itself will not be considered herein). In other words besides the plurality of projection images, a further output is supplied in the form of phase differential phase contrast images that record for each detector pixel element an associated phase gradient. Said associated phase gradient measures the phase shift caused by matter interaction of the respective ray that is incident on the respective pixel px. This is the phase gradient seen by that pixel element. See for instance, S A McDonald, "Advanced phase-contrast imaging using a grating interferometer", J. Synchrotron Rad. (2009), 16, 562-572, in particular Eq (1) on p 564.

If a conventional, energy integrating detector and a polychromatic X-ray source are used, as is indeed the case herein for a preferred embodiment, then the attenuation contrast image suffers from beam-hardening, i.e., the attenuation contrast image is not quantitative. Therefore it is proposed herein processing unit IP, configured to produce, based on one or more projection images and the one or more phase contrast images as recorded by the phase imaging apparatus 100 above, quantitative monochromatic images MC for any desired energy value E as supplied by the user through an input device such a pointer tool PT (mouse or stylus) or keyboard or touch-screen-interaction or as supplied automatically by an image processing protocol that is run on workstation CON.

In the following it is explained in more detail an approach for modeling physical interactions that give rise to the recorded imagery and that underlie operation of said image processor IP.

Initially, for each projection angle θ, the radiation signal I is picked up by each detector pixel px and said signal oscillates at a detector pixel/channel px with phase stepping x approximately as follows:

$$I(x) = A\left(1 + V\cos\left(2\pi\frac{x}{q} + \phi\right)\right) \quad (1)$$

where A is related to the attenuation of the ray, ϕ to the local phase gradient, V ("visibility") to the small angle scattering, g the pitch of grating G2 and x is the relative displacement of the grids G1 and G2 during phase stepping. Quantitative values of the physical properties are derived by relating the fitted values A, V, φ to those acquired during a blank scan $A_0$, $V_0$, $\phi_0$. In a blank or "air" scan, the scanner is operated in a calibration run where the tube XR is energized to emit an X-ray beam with an energy spectrum to be used later in the actual imaging run. In the blank scan, no imaging object PAT is present between tube and detector whereas the object is present in the actual imaging run. Said fitting is achieved in one embodiment by running a fast fast-Fourier transform (FFT) on the acquired signal I. The Fourier decomposition then yields A as the DC component, with the amplitude of A a measure for the visibility V and the phase φ is the frequency component $v=2\pi/g$. It is understood herein, that the approximation as per (1) is in general different for each pixel px as each pixel px will in general see a different fluctuation of intensity for each x so the values A, V, φ will need to be fitted separately for each pixel px.

As briefly mentioned earlier, because of the beam-hardening effect, the spectrum of the scanner IMA's X-ray beam shifts towards higher energies as it travels through matter since the attenuation decreases with energy. This change of the X-ray spectrum during the object PAT scan implies that the fitted values can no longer be directly related to those of the blank scan. If the energy dependence of all three parameters A, V, φ were known—this is the assumption in Applicant's WO 2012/029039—then the effect of beam-hardening can be resolved for. This is a reasonable approximation for the mammography energy range, where attenuation is dominated by the photo-electric effect.

However, for higher energies (for instance in the range of 50-60 keV as pursued herein in one embodiment) there is an increase in the contribution of Compton scattering to the overall attenuation. Furthermore, the relative contribution of the photo-electric effect and Compton scattering to the attenuation is not known a priori since it depends on the object PAT being scanned.

Mathematically, we can formulate the problem as an estimation problem of the parameters $p_p$, $p_C$ (representing the contribution of the photo-electric effect and Compton scattering to the linear attenuation coefficient $\mu(E,I)$, respectively), and $\phi(E_d)$ from intensity measurements at different grid positions x according to the model:

$$I(x) = \int dE I_0(E) e^{-\int \mu(E,l) dl} + \int dE V(E) I_0(E) e^{-\int \mu(E,l) dl} \cos\left(2\pi \frac{x}{q_0} + \phi(E_d)\frac{E_d}{E}\right) \quad (2)$$

with $$\int \mu(E,l) dl = p_p (E/E_d)^{-3} + p_C f_{KN}(E) \quad (3a)$$

wherein:
E is the energy range;
l is the in-tissue path length through object PAT;
I(x) is the intensity recorded at grid position x in the imaging run, whereas $dE\, I_0(E)$ is the intensity recorded at the pixel in the "air" or blank scan in the energy interval [E, E+dE];
V is the visibility, that is, the modulation depth of the interference pattern.
$E_d$ is the design (or more generally speaking a reference) energy. This is the energy at which the interferometer of FIG. 2 responds with the best visibility V. In other words, the design energy is the energy where the observed modulation depth of the interference pattern is at its maximum. This modulation depth is probed during the blank scan and is quantified by the fitted value V to the data acquired during the blank scan as explained earlier in relation to Eq (1);
x=grid position;
$p_p$, $p_C$=the respective contributions of the photoelectric effect and Compton scattering to the attenuation of the beam;
g=pitch of grating G2;
φ=phase shift caused by the imager object PAT and as recorded at the detector wired interferometric arrangement as per FIG. 2;
$f_{KN}$=the Klein-Nishina formula describing the energy dependence of the Compton scattering cross-section in the energy range at hand.

As the reconstruction step is linear we can also write the above equation in image space:

$$\mu(E, \vec{r}) = P_p(\vec{r})\left(\frac{E}{E_d}\right)^{-3} + P_C(\vec{r}) f_{KN}(E) \quad (3b)$$

together with $p_p = \int P_p(l) dl$, and $p_C = \int P_C(l) dl$.

Model equations (2),(3), can be understood as a rewrite of equation (1) where now the intensities I(.) seen at the respective grid position x for each energy are integrated over the energy spectrum of the attenuated X-ray beam as registered at the detector D.

The energy dependence of the visibility V can be modeled as a product of $V_I$ (that is, the known energy dependence of the interferometer setup such as the Talbot order n, which is related to the distance d between the grating G1 and G2 by the relation $d=n\, p_1^2/8\lambda$, where λ is the wavelength of the X-rays and n is an odd integer [other, similar formulae might apply if the grating G1 is not a π grating], grating efficiencies at different energies, etc.), and $V_o$ (that is, the yet unknown influence of the object to the visibility. The energy dependence of the later one can be modeled as $$V_o(E) = V_o(E_d)\frac{E_d^2}{E^2} \quad (4)$$

Figure 3:
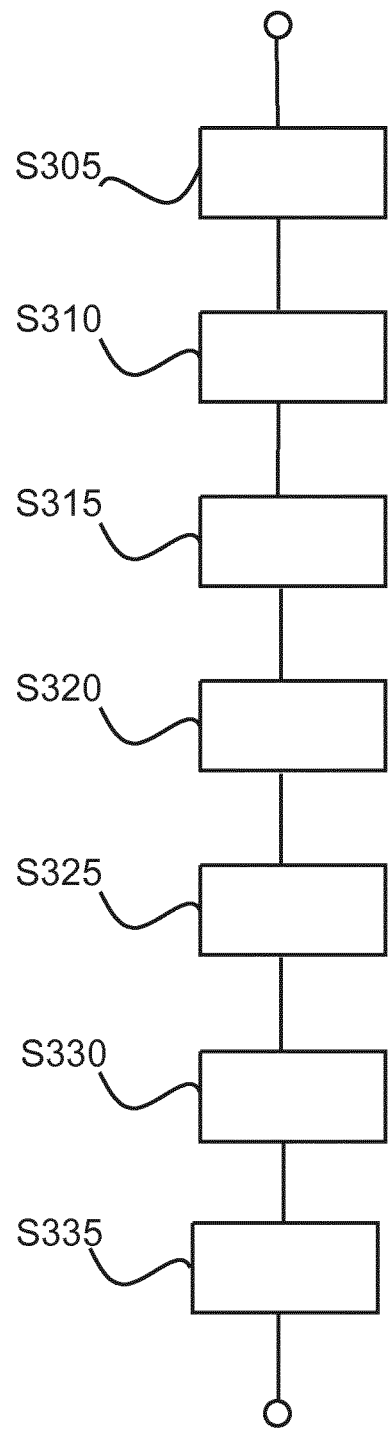
FIG. 3 shows a flow chart for a method of generating an image.

In the following, with reference to the flow chart in FIG. 3, method steps are described that are implemented by image processor IP. The method harnesses an additional bit of information about a known relationship between $p_C$ and $\phi(E_d)$ that Applicants have found out can be put to good use for the generation of monochromatic images from a tape image data detected at energy integrating detectors:

In step S305, the one or more phase contrast images are received at image processes input port IN.

Based on Eq. (1), or by using an approximation method for beam hardening correction (such as described in applicant's WO 2012/029039), initial estimates for the total attenuation, the small angle scattering, and the phase gradient at the design energy $E_d$ are derived for a radiation signal as picked up at respective one of detector pixels px.

In step S 310, using the initial estimates for the phase gradient, the line integral p of the electron density along each of ray (making up the beam XB beam incident on detector D) can be estimated, either by integration of the phase gradient, or by reconstruction of the complex refractive index δ, or by conversion to electron density using a known relationship (see Eq.(2.134) in D Paganin, "Coherent X-Ray Optics", Oxford University Press, 2006, Chapter 2):

$$\delta(E) = \frac{e^2 \rho}{2\epsilon_0 m_e c^2 k(E)^2} \quad (5)$$

wherein:
E=energy;
ρ=the electron density we wish to solve for;
δ=the refractive index of the material;
$\epsilon_0$=the dielectric constant of vacuum;
$m_e$=the mass of the electron;
k=the wave number related to the energy;
c=speed of light.

The conversion is then followed up by a numerical forward projection along the ray path to so derive a set of synthesized or estimated projection images, in general different from the actual, scanner IMA acquired projection images mentioned earlier in above in relation to FIG. 1. Alternatively in order to compute the electron density map, software packages known from X-ray crystallography may also be used with benefit.

In step S315, the line integral of the electron density can be used to compute the contribution $p_C$ of the Compton scatter to the total attenuation of the line integral p, which has been initially estimated as $p=-\ln(A/A_0)$. Consequently, the difference of the total attenuation and the estimate for $p_C$ can be used, see Eq. (3), to derive at step S320 the contribution of the photo-electric effect $p_p$. The computation of the $p_C$ contribution is may be based on a relationship as described in Alvarez et al "energy-selective reconstructions in the X-ray computerized tomography", Phys. Med. Biol., vol 21, No 5, 733-744, Eqs 2-5 on p 734, in particular Eq 2 (in Alvarez "ρ" designates mass-density whereas in Eq (5) above, ρ designates electron density). Alvarez's Eq (2), (4), (5) describe how attenuation coefficients may be linearly combined (a1,a2) from energy terms. Applicant discovered, that the following simplifying assumptions may be made without undue loss of accuracy: in human tissue, there is known to be a preponderance of elements with relatively low atomic numbers so in Alvarez's linear coefficients a1,a2 one may safely assume Z/A~0.5, where (using the Alvarez notation), "A" is the atomic weight of tissue elements. Also, mass density is proportional to electron density as there is one electron and one neutron to each proton. Therefore, once the electron density is gotten one may approximate mass density as per $\rho_m = \rho_e *(m_p + m_n)$, with $m_p$, $m_n$ designating mass of proton and neutron, respectively.

Using $p_C$ and $p_p$ in combination with the known initial spectrum of the X-ray beam, it is possible to derive the effective spectrum of the X-ray beam as recorded at the detector D. Based on Eq. (2), a more accurate estimate of the line integral of the electron density along the X-ray can be estimated. This improved electron density estimate can then be used instead of the initial estimate back in step S315 to so define an iterative loop to iteratively improve the electron density estimates.

In step S325, the values $p_p$ and $p_C$ are used to reconstruct a so-called photo-electric image $P_p$ and a Compton scatter image $P_C$, each recording the attenuations that are (solely) attributable to the respective ones of the two attenuation types. Filtered back-projection or iterative reconstruction methods may be used for this task. By proper linear combination of these two images, "monochromatic" images can be generated by simple evaluation of Eq.(3) at the desired energy E. For each pixel and projection angle, the respective contributions $p_C$ and $p_p$ are dimensionless values and represent line-integrals of the photo-electric and Compton-scatter contributions to the linear attenuation coefficient. The filtered backward projection operator FBP(.) is then applied to the "sinograms" defined by all $p_C$, $p_p$ values for each pixel and projection angle. The corresponding (for $p_C$ and $p_p$, respectively) FBP images in image space now each represent a "purified" version of the overall linear attenuation coefficient in that each now measures the respective attenuation caused solely by photon electric attenuation and Compton scattering, respectively. Given the user requested energy E, a desired mono-chromatic image MC can then linearly combined as per Eq (3) above.

In step S330, display of the so generated mono-chromatic image MC on the monitor M is effected.

According to one embodiment, modes of visualization as used in spectral imagery (such as water-bone images or water-iodine images) can be generated at user request at step S335. For instance, water-bone separation visualization can be done by the following procedure: The relative contribution of photo-electric absorption and Compton scattering to the attenuation caused by water and calcium (i.e., bone) are known and actually, they have different relative contributions. One approach is to "explain" the measured values of $p_p$ and $p_C$ by different path lengths through water and bone, respectively. Since this is done on each detector pixel, one can build up a complete "sinogram" for the chosen basis materials, in this case water and bone. The same procedure may be applied in image domain also, where the same relative contributions of photo-electric absorption and Compton scattering to the attenuation holds true for each voxel.

In order to effect the various modes of the visualizations, image processor IP as proposed herein includes visualization module VS. The module receives a user request for the specific energy E for which the monochromatic image at step S325 is to be generated for and/or the visualization request for the water-bone or water-iodine or other rendering.

The visualization module VS includes in one embodiment, a graphical user interface GUI that is displayed on screen M. The graphical user interface includes one or more panes in which the rendered image(s) MC are displayed. The graphic user interface may also include other GUI widgets, such as a slider widgets or button widgets or scroll menus etc that are responsive to manipulation by the user with the pointer tool PT such as the mouse or otherwise. The slider or bottom can be used to adjust for a desired energy value E and/or the desired visualization (water-bone, etc). In one embodiment, image processor IP responses effectively in real time to update a currently shown monochromatic image for an updated one, for the new energy and/r visualization rendering request, by repeating the previous steps S325-S330 and/or S335 once the user request is registered. Text based input means (such a keyboard) for the desired energy and/or visualization parameters are also envisaged herein.

It will be understood from the above, that steps S 315 and S320 can be reversed in some embodiments so it is first the photoelectric scattering $p_p$ contribution that is computed and then the Compton scattering $p_C$ contribution.

It will be understood from the above also, that the described method to generate monochromatic images can be implemented conveniently as an add-on to certain existing beam hardening algorithms, such as the one in Applicant's WO 2012/029039. This allows saving computing time as at least some of overlapping or similar steps can be executed for both purposes, or data generated may be buffered or execution or data may be otherwise coordinated or allocated.

Also, it will be appreciated the described method can be applied equally to the radiography imager such as a diagnostic or interventional C-arm X-ray system or apparatus where in general a single or a small plurality of images are acquired along a single or a few, discreetly spaced, projection directions only.

The image processor and its components in particular visualizer VS may be arranged as separate modules arranged in a distributed architecture and connected in a suitable communication network.

In one embodiment, image processor IP is arranged as dedicated FPGAs or as hardwired standalone chips.

In an alternate embodiment, image processor IP and its components are resident in work station CON running as software routines thereon. Image processor IP and its components may be programmed in a suitable scientific computing platform such as Matlab® or Simulink® and may be translated into C++ or C routines maintained in a library and linked when called on by work station CON's operating system.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A method for generating an X-ray image, comprising the steps of:
   receiving a phase gradient and an overall attenuation information both derived from a phase-contrast image;
   computing an electron density image based on the phase gradient information as recorded in the phase-contrast image;
   estimating, from the computed electron-density, a contribution, $p_C$, of the Compton scattering to the overall attenuation information as recorded in the phase-contrast image;
   estimating the contribution, $p_p$, of the photo-electric absorption to the overall attenuation information as recorded in the phase-contrast image; and
   for an energy specification, combining $p_C$ and $p_p$ into a mono-chromatic image.

2. The method of claim 1, further comprising:
   displaying the mono-chromatic image on the display device.

3. The method according to claim 2, further comprising:
   responsive to a request including an updated energy specification, repeating the previous step for the updated energy specification, and displaying an updated mono-chromatic image on the display device for the updated energy specification.

4. The method according to claim 2, further comprising:
   responsive to request for a visualization mode, rendering the monochromatic image or the updated mono-chromatic image accordingly and effectuating display of same on the display device.

5. The method according to claim 4, wherein the visualization mode includes water-bone image rendering or water-iodine rendering.

6. An X-ray image processing system including:
   an imaging apparatus configured to supply the phase-contrast image;
   a user input device for receiving the desired energy specification;
   a processing unit configured to process the phase-contrast image according to the method of claim 1;
   a display device for displaying the monochromatic image computed by the processing unit.

7. The image processing system according to claim 2, arranged for:
   displaying the mono-chromatic image on the display device.

8. The image processing system according to claim 6, arranged for:
   enabling a user to enter a request including an updated energy specification, repeating step responsive to said request for the updated energy specification; and
   displaying an updated mono-chromatic image on the display device for the updated energy specification.

9. The image processing system according to claim 6, arranged for:
- enabling a user to enter a request for a visualization mode; and
- rendering responsive to said request the monochromatic image or the updated mono-chromatic image accordingly and effectuating display of same on the display device.

10. The image processing system according to claim 9, arranged for:
- enabling a user to enter a request for a visualization mode including water-bone image rendering and water-iodine rendering; and
- rendering responsive to said request the monochromatic image or the updated mono-chromatic image accordingly and effectuating display of same on the display device.

11. The image processing system according to claim 6, arranged for recording the phase-contrast image using an energy integrating detector.

12. The image processing system according to claim 6, wherein the imaging apparatus is a computed tomography imaging apparatus.

13. The image processing system according to claim 6, arranged for executing within a framework of a beam-hardening correction algorithm.

14. A non-transitory computer-readable medium having stored thereon the computer program of claim 1.

* * * * *